United States Patent [19]

Desai et al.

[11] Patent Number: 6,096,331

[45] Date of Patent: Aug. 1, 2000

[54] METHODS AND COMPOSITIONS USEFUL FOR ADMINISTRATION OF CHEMOTHERAPEUTIC AGENTS

[75] Inventors: Neil P. Desai; Patrick Soon-Shiong, both of Los Angeles, Calif.

[73] Assignee: Vivorx Pharmaceuticals, Inc., Santa Monica, Calif.

[21] Appl. No.: 08/926,155

[22] Filed: Sep. 9, 1997

Related U.S. Application Data

[63] Continuation-in-part of application No. 08/720,756, Oct. 1, 1996, Pat. No. 5,916,596, which is a continuation-in-part of application No. 08/485,448, Jun. 7, 1995, Pat. No. 5,665,382, which is a continuation-in-part of application No. 08/200,235, Feb. 22, 1994, Pat. No. 5,498,421, which is a continuation-in-part of application No. 08/023,698, Feb. 22, 1993, Pat. No. 5,439,686, and a continuation-in-part of application No. 08/035,150, Mar. 26, 1993, Pat. No. 5,362,478.

[51] Int. Cl.[7] .................................................. A61K 9/127

[52] U.S. Cl. ........................ 424/422; 424/489; 424/426; 424/455; 424/428

[58] Field of Search ...................................... 424/450, 422, 424/489, 426, 491, 497; 514/44, 359, 358

[56] References Cited

U.S. PATENT DOCUMENTS

| | | | |
|---|---|---|---|
| 5,565,478 | 10/1996 | Kohn et al. .............................. | 514/359 |
| 5,626,862 | 5/1997 | Brem et al. .............................. | 424/426 |
| 5,731,334 | 3/1998 | Wrasidlo .................................. | 514/358 |
| 5,744,460 | 4/1998 | Müller et al. ............................. | 514/44 |

*Primary Examiner*—Thurman K. Page
*Assistant Examiner*—William E. Benston, Jr.
*Attorney, Agent, or Firm*—Gray Cary Ware & Freidenrich; Stephen E. Reiter

[57] ABSTRACT

In accordance with the present invention, there are provided compositions and methods useful for the in vivo delivery of a pharmaceutically active agent, wherein the agent is associated with a polymeric biocompatible material.

57 Claims, No Drawings

METHODS AND COMPOSITIONS USEFUL FOR ADMINISTRATION OF CHEMOTHERAPEUTIC AGENTS

RELATED APPLICATIONS

This application is a continuation-in-part of U.S. Ser. No. 08/720,756, filed Oct. 1, 1996, now issued as U.S. Pat. No. 5,916,596, and U.S. Ser. No.08/485,448, filed Jun. 7, 1995, now U.S. Pat. No. 5,665,382, which is, in turn, a continuation-in-part of U.S. Ser. No. 08/200,235, filed Feb. 22, 1994, now issued as U.S. Pat. No. 5,498,421, which is, in turn, a continuation-in-part of U.S. Ser. No. 08/023,698, filed Feb. 22, 1993, now issued as U.S. Pat. No. 5,439,626, and U.S. Ser. No. 08/035,150, filed Mar. 26, 1993, now issued as U.S. Pat. No. 5,362,478, the contents of each of which are hereby incorporated by reference in their entirety.

FIELD OF THE INVENTION

The present invention relates to in vivo delivery of biologics such as the anticancer drug paclitaxel. The invention relates to the method of use and preparation of compositions (formulations) of drugs such as the anticancer agent paclitaxel. In one aspect, the formulation of paclitaxel, known as Capxol, has been found to be significantly less toxic and more efficacious than TAXOL, a commercially available formulation of paclitaxel. In another aspect, the novel formulation Capxol, has been found to localize in certain tissues after parenteral administration, thereby increasing the efficacy of treatment of cancers associated with such tissues.

BACKGROUND OF THE INVENTION

Taxol is a naturally occurring compound which has shown great promise as an anti-cancer drug. For example taxol has been found to be an active agent against drug-refractory ovarian cancer by McGuire et al. See "Taxol: A unique Anti-Neoplastic Agent With Significant Activity Against Advanced Ovarian Epithelial Neoplasms." Ann. Int. Med., 111, 273–279 (1989). All patents, scientific articles, and other documents mentioned herein are incorporated by reference as if reproduced in full below.

Unfortunately, taxol has extremely low solubility in water, which makes it difficult to provide a suitable dosage form. In fact, in Phase I clinical trials, severe allergic reactions were caused by the emulsifiers administered in conjunction with taxol to compensate for taxol's low water solubility; at least one patient's death was caused by an allergic reaction induced by the emulsifiers. Dose limiting toxicities include neutropenia, peripheral neuropathy, and hypersensitivity reactions (HSRs).

Brown et al., in "A Phase I Trial of Taxol Given by A 6-Hour Intravenous Infusion" J of Clin Oncol, Vol. 9 No. 7, pp. 1261–1267 (July 1991) report on a Phase I Trial in which taxol was provided as a 6 -hour IV infusion every 21 days without premedication. 31 patients received 64 assessable courses of taxol. One patient had a severe (or acute) hypersensitivity reaction, which required discontinuation of the infusion and immediate treatment to save the patient's life. Another patient experienced a hypersensitivity reaction, but it was not so sever as to require discontinuing the infusion. Myelosuppression was dose-limiting, with 2 fatalities due to sepsis. Non-hematologic toxicity was of Grade 1 and 2, except for one patient with Grade 3 mucositis and 2 patients with Grade 3 neuropathy. The neuropathy consisted of reversible painful paresthesias, requiring discontinuation of taxol in two patients. Four partial responses were seen (3 in patients with non-small-cell lung cancer, and one in a patient with adenocarcinoma of unknown primary). The maximum tolerated dose reported was 275 $mg/m^2$, and the recommended Phase II starting dose was 225 $mg/m^2$. The incidence of hypersensitivity reaction was reported to be schedule-dependent, with 6 to 24-hour infusions of drug having a 0% to 8% incidence of hypersensitivity reactions. It was also reported that hypersensitivity reactions persist with or without premedication, despite prolongation of infusion times. Since these Phase I studies were conducted on terminally ill patients suffering from a variety of cancer, the efficacy of the taxol treatments could not be determined.

In a study by Kris et al, taxol formulated with Cremaphor EL in dehydrated alcohol was given as a 3-hour IV infusion every 21 days, with the administered dosage ranging from 15 to 230 $mg/m^2$ in nine escalation steps. Kris et al. concluded that "with the severity and unpredictability of the hypersensitivity reactions, further usage of taxol is not indicated with this drug formulation on this administration schedule." See Cancer Treat. Rep., Vol. 70, No. 5, May 1986.

Since early trials using a bolus injection or short (1–3 hour) infusions induced anaphylactic reactions or other hypersensitivity responses, further studies were carried out in which taxol was administered only after premedication with steroids (such as dexamethasone), antihistamines (such as diphenhydramine), and H2-antagonists (such as cimetidine or ranitidine), and the infusion time was extended to 24 hours in an attempt to eliminate the most serious allergic reactions. Various Phase I and Phase II study results have been published utilizing 24-hour infusions of taxol with maximum total dosages of 250 mg/m2, generally with the course being repeated every 3 weeks. Patients were pretreated with dexamethasone, diphenhydramine, and cimetidine to offset allergic reactions. See Einzig, et al., "Phase II Trial of Taxol in Patients with Metastatic Renal Cell Carcinoma," Cancer Investigation, 9(2) 133–136 (1991), and A. B. Miller et al., "Reporting Results of Cancer Treatment," Cancer, Vol 47, 207–214 (1981).

Koeller et al., in "A Phase I Pharmacokinetic Study of Taxol Given By a Prolonged Infusion Without Premedication," Proceedings of ASCO, Vol. 8 (March, 1989), recommends routine premedication in order to avoid the significant number of allergic reactions believed to be caused by the cremophor (polyethyoxylated castor oil) vehicle used for taxol infusion. Patients received dosages ranging from 175 $mg/m^2$ to 275 $mg/m^2$.

Wiernik et al. in "Phase I Clinical and Pharmacokinetic Study of Taxol," Cancer Research, 47, 2486–2493 (May 1, 1987), also report the administration of taxol in a cremophor vehicle by IV infusion over a 6-hour period in a Phase I study. Grade 3–4 hypersensitivity reactions incurred in 4 of 13 courses. The starting dose for the study was 15 $mg/m^2$ (one-third of the lowest toxic dose in dogs). Doses were escalated, and a minimum of 3 patients were treated at each dose level until toxicity was identified, and then 4–6 patients were treated at each subsequent level. The study concluded that neurotoxicity and leukopenia were dose-limiting, and the recommended Phase II trial dose was 250 $mg/m^2$ with premedication.

Other exemplary studies on taxol include: Legha et al., "Phase II Trail of Taxol in Metastatic Melanoma," Vol. 65 (June 1990) pp. 2478–2481; Rowinsky et al., "Phase I and Pharmacodynamic Study of Taxol in Refractory Acute Leukemias," Cancer Research, 49, 4640–4647 (Aug. 15, 1989); Grem et al., "Phase I Study of Taxol Administered as a Short IV Infusion Daily For 5 Days," Cancer Treatment Reports, Vol. 71 No. 12, (December, 1987); Donehower et al., "Phase I Trial of Taxol in Patients With Advanced Cancer," Cancer Treatment Reports, Vol, 71, No. 12, (December, 1987); Holmes et al., "Phase II Study of Taxol in Patients (PT) with Metastatic Breast Cancer (MBC)," Proceedings of the American Society of Clinical Oncology, Vol. 10, (March, 1991), pp. 60. See also Suffness. "Development of Antitumor Natural Products at the National Cancer Institute," Gann Monograph or Cancer Research, 31 (1989) pp. 21–44 (which recommends that taxol only be given as a 24-hour infusion).

Weiss et al, in "Hypersensitivity Reactions from Taxol," Journal of Clinical Oncology, Vol. 8, No. 7 (July 1990) pp. 1263–1268, reported that it was difficult to determine a reliable overall incidence of hypersensitivity reactions, HSRs, because of the wide variations in taxol doses and schedules used, and the unknown degree of influence that changing the infusion schedule and using premedication has on HSR incidents. For example, of five patients who received taxol in a 3-hour infusion at greater that 190 mg/m$^2$ with no premedication, three had reactions, while only one out of 30 patients administered even higher doses over a 6-hour infusion with no premedication had a reaction. Therefore, this suggests that prolonging the infusion to beyond 6 hours is sufficient to reduce HSR incidents. Nevertheless, Weiss et al. found that patients receiving 250 mg/m$^2$ of taxol administered via a 24-hour infusion still had definite HSRs. Thus, while prolonging drug infusion to 6 or 24-hours may reduce the risk for an acute reaction, this conclusion can not be confirmed, since 78% of the HSR reactions occurred within ten minutes of initiating the taxol infusion, which indicates that the length of time planned for the total infusion would have no bearing. Further, concentration of taxol in the infusion may also not make a difference since substantial number of patients had reactions to various small taxol dosages. Finally, not only is the mechanism of taxol HSR unknown, it is also not clear whether taxol itself is inducing HSRs, or if the HSRs are due to the excipient (Cremaphor EL; Badische Anilin und Soda Fabrik AG [BASF], Ludwigshafen, Federal Republic of Germany). Despite the uncertainty as to whether or not premedication had any influence on reducing the severity or number of HSRs, prophylactic therapy was recommended, since there is no known danger from its use.

The conflicting recommendations in the prior art concerning whether premedication should be used to avoid hypersensitivity reactions when using prolonged infusion durations, and the lack of efficacy data for infusions done over a six-hour period has led to the use of a 24-hour infusion of high doses (above 170 mg/m$^2$) of taxol in a Cremaphor EL emulsion as an accepted cancer treatment protocol.

Although it appears possible to minimize the side effects of administering taxol in an emulsion by one of a long infusion duration, the long infusion duration is inconvenient for patients, and is expensive due to the need to monitor the patients for the entire 6 to 24-hour infusion duration. Further, the long infusion duration requires that patients spend at least one night in a hospital or treatment clinic.

The use of higher doses of paclitaxel has also been described in the literature. To determine the maximal-tolerated dose (MTD) of paclitaxel in combination with high-dose cyclophosphamide and cisplatin followed by autologous hematopoietic progenitor-cell support (AHPCS), Stemmer et al (Stemmer S M, Cagnoni P J, Shpall E J, et al: High-dose paclitaxel, cyclophophamide, and cisplatin with autologous hematopoietic progenitor-cell support: A phase I trial. J Clin Oncol 14:1463–1472, 1996) have conducted a phase I trial in forty-nine patients with poor-prognosis breast cancer, non-Hodgkin's lymphoma (NHL) or ovarian cancer with escalating doses of paclitaxel infused over 24 hours, followed by cyclophosphamide (5,625 mg/m$^2$) and cisplatin (165 mg/m$^2$) and AHPCS. Dose-limiting toxicity was encountered in two patients at 825 mg/m$^2$ of paclitaxel; one patient died of multi-organ failure and the other developed grade 3 respiratory, CNS, and renal toxicity, which resolved. Grade 3 polyneuropathy and grade 4 CNS toxicity were also observed. The MTD of this combination was determined to be paclitaxel (775 mg/m$^2$), cyclophosphamide (5,625 mg/m$^2$), and cisplatin (165 mg/m$^2$) followed by AHPCS. Sensory polyneuropathy and mucositis were prominent toxicities, but both were reversible and tolerable. Eighteen of 33 patients (54%) with breast cancer achieved a partial response. Responses were also observed in patients with NHL (four of five patients) and ovarian cancer (two of two patients).

U.S. Pat. No. 5,641,803 reports the use of Taxol at doses of 175 and 135 mg/m$^2$, administered in a 3 hour infusion. The infusion protocols require the use of premedication and reports the incidences of hypersensitivity reactions in 35% of the patients. Neurotoxicity was reported in 51% of the patients, with 66% of patients experiencing neurotoxicity in the high dose group and 37% in the low dose group. Furthermore, it was noted that 48% of the patients experienced neurotoxicity for longer infusion times of 24 hours while 54% of patients experienced neurotoxicity for the shorter 3 hour infusion.

There is evidence in the literature that higher doses of paclitaxel result in a higher response rate. The optimal doses and schedules for paclitaxel are still under investigation. To assess the possibility that paclitaxel dose intensity may be important in the induction of disease response, Reed et al of NCI (Reed E, Bitton R, Sarosy G, Kohn E: Paclitaxel dose intensity. Journal of Infusional Chemotherapy 6:59–63, 1996) analyzed the available phase II trial data in the treatment of ovarian cancer and breast cancer. Their results suggest that the relationship between objective disease response and paclitaxel dose intensity in recurrent ovarian cancer is highly statistically significant with two-side p value of 0.022. The relationship in breast cancer is even stronger, with a two-sided p value of 0.004. At 135 mg/m$^2$/21 days, the objective response rate was 13.2%; and at 250 mg/m$^2$/21 days, the objective response rate was 35.9%. The response rate seen at the intermediate dose of 175 mg/m$^2$ was linear with the 135 mg/m$^2$ and 250 mg/m$^2$ results and the linear regression analysis shows a correlation coefficient for these data of 0.946 (Reed et al, 1996).

In a study by Holmes (Holmes F A, Wasters R S, Theriault R L, et al: Phase II trial of Taxol, an active drug in the treatment of metastatic breast cancer. J Natl Cancer Inst 83:1797–1805, 1991), and at MSKCC (Reichman B S, Seidman A D, Crown J P A, et al: Paclitaxel and recombinant human granulocyte colony-stimulating factor as initial chemotherapy for metastatic breast cancer. J Cin Oncol 11:1943–1951, 1993), it was shown that higher doses of TAXOL up to 250 mg/m$^2$ produced greater responses (60%) than the 175 mg/m$^2$ dose (26%) currently approved for TAXOL. These results, however, have not been reproduced due to higher toxicity at these higher doses. These studies, however, bear proof to the potential increase in response rate at increased doses of paclitaxel.

Since premedication is required for the administration of Taxol, often necessitating overnight stays of the patient at the hospital, it is highly desirable to develop formulations of paclitaxel that obviate the need for premedication.

Since premedication is required for the administration of Taxol, due to HSR's associated with administration of the drug, it is highly desirable to develop a formulation of paclitaxel that does not cause hypersensitivity reactions. It is also desirable to develop formulations of paclitaxel that do not cause neurotoxicity.

Since Taxol infusions are generally preceded by premedication, and require post-infusion monitoring and record keeping, often necessitating overnight stays of the patient at the hospital, it is highly desirable to develop a formulation of paclitaxel which would allow for recipients to be treated on an out-patient basis.

Since it has been demonstrated that higher doses of Taxol achieve improved clinical responses albeit with higher toxicity, it is desirable to develop a formulation of paclitaxel which can achieve these doses without this toxicity.

Since it has been demonstrated that the dose limiting toxicity of Taxol is cerebral and neurotoxicity, it is desirable to develop a formulation of paclitaxel that decreases such toxicity.

It is also desirable to eliminate the need to use premedication since this increases patient discomfort and increases the expense and duration of treatment.

It is also desirable to shorten the duration required for the infusion of Taxol (currently administered in 3–24 hours) to minimize patient stay at the hospital or clinc.

Since Taxol is currently approved for administration at concentrations between 0.6–1.2 mg/ml and a typical dose in humans is about 250–350 mg, this results in infusion volumes typically greater than 300 ml. It is desirable to reduce these infusion volumes. This can be done by the development of formulations of paclitaxel that are stable at higher concentrations so as to reduce the time of administration.

BREIF DESCRIPTION OF THE INVENTION

The anticancer agent paclitaxel (TAXOL, Bristol Myers Squibb, BMS,) has remarkable clinical activity in a number of human cancers including cancers of the ovary, breast, lung, esophagus, head and neck region, bladder and lymphomas. It is currently approved for the treatment of ovarian carcinoma where it is used in combination with cisplatin and for metastatic breast cancer that has failed prior treatment with one combination chemotherapy regimen. The major limitation of Taxol is its poor solubility and consequently the BMS formulation contains 50% Cremaphor EL and 50% ethanol as the solubilizing vehicle. Prior to intravenous administration, this formulation must be diluted 1:10 in saline for a final dosing solution containing 0.6 mg/ml of paclitaxel. This formulation has been linked to severe hypersensitivity reactions in animals (Lorenz et al., *Agents Actions* 1987, 7, 63–67) and humans (Weiss et al., *J. Clin. Oncol.* 1990, 8, 1263–63) and consequently requires premedication of patients with corticosteroids (dexamethasone) and antihistamines. The large dilution results in large volumes of infusion (typical dose 175 mg/m$^2$) upto 1 liter and infusion times ranging from 3 hours to 24 hours. Thus, there is a need for an alternative less toxic formulation for paclitaxel.

Capxol™ is a novel, cremophor-free formulation of the anticancer drug paclitaxel. The inventors, based on animal studies, believe that a cremophor-free formulation will be significantly less toxic and will not require premedication of patients. Premedication is necessary to reduce the hypersensitivity and anaphylaxis that occurs as a result of cremophor in the currently approved and marketed BMS (Bristol Myers Squibb) formulation of paclitaxel. Capxol™ is a lyophilized powder for reconstitution and intravenous administration. When reconstituted with a suitable aqueous medium such as 0.9% sodium chloride injection or 5% dextrose injection, Capxol™ forms a stable colloidal solution of paclitaxel. The size of the collodial suspension may range from 20 nm to 8 microns with a preferred range of about 20–400 nm. The two major components of Capxol™ are unmodified paclitaxel and human serum albumin (HSA). Since HSA is freely soluble in water, Capxol™ can be reconstituted to any desired concentration of paclitaxel limited only by the solubility limits for HSA. Thus Capxol™ can be reconstituted in a wide range of concentrations ranging from dilute (0.1 mg/ml paclitaxel) to concentrated (20 mg/ml paclitaxel). This can result in fairly small volumes of administration.

In accordance with the present invention, there are provided compositions and methods useful for in vivo delivery of biologics, in the form of nanoparticles that are suitable for parenteral administration in aqueous suspension. Invention compositions comprise drugs, such as paclitaxel, stabilized by a polymer. The polymer is a biocompatible material, such as the protein albumin. Use of invention compositions for the delivery of biologics obviates the necessity for administration of biologics in toxic diluents of vehicles, for example, ethanol and polyethoxylated castor oil, diluted in normal saline (see, for example, Norton et al., in Abstracts of the 2nd National Cancer Institute Workshop on Taxol & Taxus, Sep. 23–24, 1992). A disadvantage of such known compositions is their propensity to produce severe allergic and other side effects.

It is known that the delivery of biologics in the form of a particulate suspension allows targeting to organs such as the liver, lungs, spleen, lymphatic circulation, and the like, due to the uptake in these organs, of the particles by the reticuloenodothelial (RES) system of cell. Targeting to the RES containing organs may be controlled through the use of particles of varying size, and through administration by different routes. But when administered to rats, Capxol was unexpectedly and surprisingly found to accumulate in tissues other than those containing the RES such as the prostate, pancreas, testes, seminiferous tubules, bone, etc. to a significantly greater level than Taxol at similar doses.

Thus, it is very surprising that the invention formulation of paclitaxel, Capxol, a nanoparticle formulation, concentrates in tissues such as the prostate, pancreas, testes, seminiferous tubules, bone, etc., i.e., in organs not containing the RES, at a significantly higher level than a non-particulate formulation of paclitaxel such as Taxol. Thus, Capxol may be utilized to treat cancers of these tissues with a higher efficacy than Taxol. However, the distribution to many other tissues is similar for Capxol and Taxol, therefore Capxol is expected to maintain anticancer activity at least equal to that of TAXOL in other tissues.

The basis for the localization within the prostate could be a result of the particle size of the formulation (20–400 nm), or the presence the protein albumin in the formulation which may cause localization into the prostatic tissue through specific membrane receptors (gp 60, gp 18, gp 13 and the like). It is also likely that other biocompatible, biodegradable polymers other than albumin may show specificity to certain tissues such as the prostate resulting in high local concentration of paclitaxel in these tissues as a result of the properties described above. Such biocompatible materials are contemplated within the scope of this invention. A preferred embodiment of a composition to achieve high local concentrations of paclitaxel in the prostate is a formulation containing paclitaxel and albumin with a particle size in the range of 20–400 nm, and free of cremophor. This embodiment has also been demonstrated to result in higher level concentrations of paclitaxel in the, pancreas, kidney, lung, heart, bone, and spleen when compared to Taxol at equivalent doses. These properties provide novel applications of this formulation of paclitaxel including methods of lowering testosterone levels, achieving medical orchiectomy, providing high local concentrations to coronary vasculature for the treatment of restenosis.

It is also very surprising that paclitaxel is metabolized into its metabolites at a much slower rate than Taxol when administered as Capxol. This enables increased and sustained anticancer activity for longer periods with similar doses of paclitaxel.

It is also very surprising that when Capxol and Taxol are administered to rats at equivalent doses of paclitaxel, a much higher degree of myelosuppression results for the Taxol group compared to the Capxol group. This can result in lower indicidences of infections and fever episodes (e.g., febrile neutropenia). It can also reduce the cycle time in between treatments which is currently 21 days. Thus the use of Capxol may provide substantial advantage over Taxol.

It was surprisingly found that the Taxol vehicle, Cremophor/Ethanol diluted in saline, alone caused severe hypersensitivity reactions and death in several dose groups of mice. No such reactions were observed for the Capxol groups at equivalent and higher doses. Thus Capxol, a formulation of paclitaxel that is free of the Taxol vehicle is of substantial advantage.

It is also very surprising that when Capxol and Taxol are administered to rats at equivalent doses of paclitaxel, a much lower toxicity is seen for the Capxol compared to Taxol as evidenced by significantly higher LD50 values. This may allow for higher more therapeutically effective doses of paclitaxel to be administered to patients. There is evidence in the literature showing increases response rates to higher doses of paclitaxel. The Capxol formulation may allow the administration of these higher doses due to lower toxicity and thereby exploit the full potential of this drug.

Surprisingly, the Capxol formulations show an increased efficacy when compared to TAXOL. In addition, higher doses of paclitaxel are achieved in the Capxol groups due to lower toxicity of the formulation. These high doses can be administered as bolus injections.

It is also surprising that Capxol, a formulation of the substantially water-insoluble drug, paclitaxel, is stable when reconstituted in an aqueous medium at several different concentrations ranging from, but not limited to 0.1–20 mg/ml. This offers substantial advantage over Taxol during administration of the drug as it results in smaller infusion volumes, overcomes instability issues known for Taxol, such as precipitation, and avoids the use of an in-line filter in the infusion line. Thus Capxol greatly simplifies and improves the administration of paclitaxel to patients.

It is also surprising that Capxol when administered to rats at equivalent doses of paclitaxel as Taxol, shows no sign of neurotoxicity while Taxol even at low doses shows neurotoxic effects.

The invention formulation further allows the administration of paclitaxel, and other substantially water insoluble pharmacologically active agents, employing a much smaller volume of liquid and requiring greatly reduced administration time relative to administration volumes and times required by prior art delivery systems.

In combination with a biocompatible polymer matrix, the invention formulation (Capxol) allows for local sustained delivery of paclitaxel with lower toxicity and prolonged activity.

The above surprising findings for Capxol offer the potential to substantially improve the quality of life of patients receiving paclitaxel.

Potential Advantages of the Capxol™ formulation for Paclitaxel

Capxol™ is a lyophilized powder containing paclitaxel and human serum albumin. Due to the nature of the colloidal solution formed from reconstitution of the lyophilized powder toxic emulsifiers such as cremophor (in the BMS formulation of paclitaxel) or polysorbate 80 (as in the Rhone Poulenc formulation of docetaxel) and solvents such as ethanol to solubilize the drug are not required. Removing toxic emulsifiers will reduce the incidences of severe hypersensitivity and anaphylactic reactions that are known to occur in products TAXOL.

In addition, no premedication with steroids and antihistamines are anticipated prior to administration of the drug.

Due to reduced toxicities, as evidenced by the $LD_{10}/LD_{50}$ studies, higher doses may be employed for greater efficacy.

The reduction in myelosuppression (as compared with the BMS formulation) is expected to reduce the period of the treatment cycle (currently 3 weeks) and improve the therapeutic outcomes.

Capxol™ can be administered at much higher concentrations (up to 20 mg/ml) compared with the BMS formulation (0.6 mg/ml), allowing much lower volume infusions, and administration as an intravenous bolus.

TAXOL may be infused only with nitroglycerin polyolefin infusion sets due to leaching of plasticizers from standard infusion tubing into the formulation. Capxol shows no leaching and may be utilized with any standard infusion tubing. In addition, only glass or polyolefin containers are to be used for storing all cremophor containing solutions. The Capxol formulation has no such limitations.

A recognized problem with TAXOL formulation is the precipitation of paclitaxel in indwelling catheters. This results in erratic and poorly controlled dosing. Due to the inherent stability of the colloidal solution of the new formulation, Capxol™, the problem of precipitation is alleviated.

The administration of Taxol requires the use of in line filters to remove precipitates and other particulate matter. Capxol has no such requirement due to inherent stability.

The literature suggests that particles in the low hundred nonometer size range preferentially partition into tumors through leaky blood vessels at the tumor site. The colloidal particles of paclitaxel in the Capxol™ formulation may therefore show a preferential targeting effect, greatly reducing the side effects of paclitaxel administered in the BMS formulation.

Therefore, it is a primary object of the present invention to provide a new formulation of paclitaxel that provides the above desirable characteristics.

It is another object of the present invention to provide a new formulation of paclitaxel that localizes paclitaxel in certain tissues, thereby providing higher anticancer activity at these sites.

It is another object of the invention to administer paclitaxel at concentrations greater than about 2 mg/ml in order to reduce infusion volumes.

It is also an object of the invention to provide a formulation of paclitaxel that is free of the Taxol vehicle.

It is yet another object of the invention to provide a formulation of paclitaxel that improves the quality of life of patients receiving Taxol for the treatment of cancer.

DETAILED DESCRIPTION OF THE INVENTION

In accordance with the present invention, there are provided compositions for in vivo delivery of a biologic. As used herein, the term "in vivo delivery" refers to delivery of a biologic by such routes of administration as oral, intravenous, subcutaneous, intrapertioneal, intrathecal, intramuscular, intracranial, inhalational, topical, transdermal, suppository (rectal), pessary (vaginal), and the like.

As used herein, the term "biologic" refers to pharmaceutically active agents (such as analgesic agents, anesthetic agents, anti-asthamatic agents, antibiotics, anti-depressant agents, anti-diabetic agents, anti-fungal agents, anti-hypertensive agents, anti-inflammatory agents, anti-neoplastic agents, anxiolytic agents, enzymatically active agents, nucleic acid constructs, immunostimulating agents, immunosuppressive agents, physiologically active gases, vaccines, and the like), diagnostic agents (such as ultrasound contrast agents, radiocontrast agents, or magnetic contrast agents), agents of nutritional value, and the like.

As used herein, the term "micron" refers to a unit of measure of one one-thousandth of a millimeter. The term "nono-" refers to dimensions that are less than 1 micron.

A number of biocompatible material may be employed in the practice of the present invention for the formation of a plymeric shell. As used herein, the term "biocompatible" describes a substance that does not appreciably alter or affect in any adverse way, the biological system into which it is introduced. A presently preferred polymeric for use in the formation of a shell is the protein albumin. Other suitable biocompatible material maybe utilized in the present formulation and these have been discussed in detail in related applications.

Several biocompatible materials may be employed in the practice of the present invention for the formation of a polymeric shell. For example, naturally occurring biocompatible materials such as proteins, polypeptides, oligopeptides, polynucleotides, polysaccharides (e.g., starch, cellulose, dextrans, alginates, chitosan, pectin, hyaluronic acid, and the like), lipids, and so on, are candidates for such modification.

As examples of suitable biocompatible materials, naturally occurring or synthetic proteins may be employed, Examples of suitable proteins include albumin (which contains 35 cysteine residues), insulin (which contains 6 cysteines), hemoglobin (which contains 6 cysteine residues per $a_2\beta_2$ unit), lysozyme (which contains 8 cysteine residues), immunoglobulins, a-2-macroglobulin, fibronectin, vitronectin, fibrinogen, casein and the like, as well as combinations of any two or more thereof.

A presently preferred protein for use in the formation of a polymeric shell is albumin. Optionally, proteins such as a-2-macroglobulin, a known opsonin, could be used to enhance uptake of the shell encased particles of biologic by macrophase-like cells, or to enhance the uptake of the shell encased particles into the liver and spleen. Other ligands such as glycoproteins may also enhance uptake into certain tissues. Other functional proteins, such as antibodies or enzymes, which could facilitate targeting of biologic to a desired site, can also be used in the formation of the polymeric shell.

Similarly, synthetic polymers are also good candidates for preparation of the drug formulation. Examples include polyalkylene glycols (e.g., linear or branched chain), polyvinyl alcohol, polyacrylates, polyhydroxyethyl methacrylate, polyacrylic acid, polyethyloxazoline, polyacrylamides, polyisopropyl acrylamides, polyvinyl pyrrolidinone, polylactide/glycolide and the like, and combinations thereof, are good candidates for the biocompatible polymer in the invention formulation.

These biocompatible materials may also be employed in several physical forms such as gels, crosslinked or uncrosslinked to provide matrices from which the pharmacologically active ingredient, for example paclitaxel, may be released by diffusion and/or degradation of the matrix. Temperature sensitive materials may also be utilized as the dispersing matrix for the invention formulation. Thus for example, the Capxol may be injected in a liquid formulation of the temperature sensitive material (e.g., copolymers of polyacrylamides or copolymers of polyalkylene glycols and polylactide/glycolides) which gel at the tumor site and provide slow release of Capxol. The Capxol formulation may be dispersed into a matrix of the above mentioned biocompatible polymers to provide a controlled release formulation of paclitaxel, which through the properties of the Capxol formulation (albumin associated with paclitaxel) results in lower toxicity to brain tissue as well as lower systemic toxicity as discussed below. This combination of Capxol or other chemotherapeutic agents formulated similar to Capxol together with a biocompatible polymer matrix may be useful for the controlled local delivery of chemotherapeutic agents for treating solid tumors in the brain and peritoneum (ovarian cancer) and in local applications to other solid tumors. These combination formulations are not limited to the use of paclitaxel and may be utilized with a wide variety of pharmacologically active ingredients including antiinfectives, immunosuppressives and other chemotherapeutics and the like.

In the preparation of invention compositions, one can optionally employ a dispersing agent to suspend or dissolve biologic. Dispersing agents contemplated for use in the practice of the present invention include any liquid that is capable of suspending or dissolving biologic, but does not chemically react with either the polymer employed to produce the shell, or the biologic itself. Examples include water, vegetable oils, (e.g., soybean oil, mineral oil, corn oil, rapeseed oil, coconut oil, olive oil, safflower oil, cotton seed oil, and the like), aliphatic, cycloaliphatic, or aromatic hydrocarbons having 4–30 carbon atoms (e.g., n-dodecane, n-decane, n-hexane, cyclohexane, toluene, benzene, and the like), aliphatic or aromatic alcohols having 1–30 carbon atoms (e.g., octanol, and the like), aliphatic or aromatic esters having 2–30 carbon atoms (e.g., ethyl capyrlate (octanoate), and the like), alkyl, aryl, or cyclic ethers having 2–30 carbon atoms (e.g., diethyl ether, tetrahydrofuran, and the like), alkyl or aryl halides having 1–30 carbon atoms (and optionally more than one halogen substituent, e.g., $CH_3Cl$, $CH_2Cl_2$, $CHCl_3$, $CH_2Cl-CH_2Cl$, and the like), ketones having 3–30 carbon atoms (e.g., acetone, methyl ethyl ketone, and the like), polyalkylene glycols (e.g., polyethylene glycol, and the like), or combinations of any two or more thereof.

Especially preferred combinations of dispersing agents include volatile liquids such as dichloromethane, chloroform, ethyl acetate, benzene, and the like (i.e., solvents that have a high degree of solubility for the pharmacologically active agent, and are soluble in the other dispersing agent employed), along with a less volatile dispersing agent. When added to the other dispersing agent, these volatile additives help to drive the solubility of the pharmacologically active agent into the dispersing agent. This is desirable since this step is usually time consuming. Following dissolution, the volatile component may be removed by evaporation (optionally under vacuum).

Particles of biologic substantially completely contained within a polymeric shell, or associated therewith, prepared as described herein, are delivered neat, or optionally as a suspension in a biocompatible medium. This medium may be selected from water, buffered aqueous media, saline, buffered saline, optionally buffered solutions of amino acids, optionally buffered solutions of proteins, optionally buffered solutions of sugars, optionally buffered solutions of carbohydrates, optionally buffered solutions of vitamins, optionally buffered solutions of synthetic polymers, lipid-containing emulsions, and the like.

In addition, the polymeric shell can optionally be modified by a suitable agent, wherein the agent is associated with the polymeric shell through an optional covalent bond. Covalent bonds contemplated for such linkages include ester, ether, urethane, diester, amide, secondary or tertiary amine, phosphate ester, sulfate ester, and the like bonds. Suitable agents contemplated for this optional modification of the polymeric shell include synthetic polymers (polyalkylene glycols (e.g., linear or branched chain polyethylene glycol), polyvinyl alcohol, polyhydroxyethyl methacrylate, polyacrylic acid, polyethyloxazoline, polyacrylamide, polyvinyl pyrrolidinone, and the like), phospholipids (such as phosphatidyl choline (PC), phosphatidyl ethanolamine (PE), phosphatidyl inositol (PI), sphingomyelin, and the like), proteins (such as enzymes, antibodies, and the like), polysaccharides (such as starch, cellulose, dextrans, alginates, chitosan, pectin, hyaluronic acid, and the like), chemical modifying agents (such as pyridoxal 5'-phosphate, derivatives of pyridoxal, dialdehydes, diaspirin esters, and the like), or combinations of any two or more thereof.

Variations on the general theme of dissolved biologic enclosed within a polymeric shell are possible. A suspension of fine particles of biologic in a biocompatible dispersing agent could be used (in place of a biocompatible dispersing agent containing dissolved biologic) to produce a polymeric shell containing dispersing agent-suspended particles of biologic. In other words, the polymeric shell could contain a saturated solution of biologic in dispersing agent. Another variation is a polymeric shell containing a solid core of biologic produced by initially dissolving the biologic in a volatile organic solvent (e.g. benzene), forming the polymeric shell and evaporating the volatile solvent under vacuum, e.g., in an evaporator, spray drier or freeze-drying the entire suspension. This results in a structure having a solid core of biologic surrounded by a polymer coat. This latter method is particularly advantageous for delivering high doses of biologic in a relatively small volume. In some cases, the biocompatible material forming the shell about the core could itself be a therapeutic or diagnostic agent, e.g., in the case of insulin, which may be delivered as part of a polymeric shell formed in the process described above. In other cases, the polymer forming the shell could participate in the delivery of a biologic, e.g., in the case of antibodies used for targeting, or in the case of hemoglobin, which may be delivered as part of a polymeric shell formed in the ultrasonic irradiation process described above, thereby providing a blood substitute having a high binding capacity for oxygen.

In accordance with a specific embodiment of the present invention, there are provided pharmaceutically acceptable formulations of paclitaxel useful for the treatment of primary tumors in a subject, which formulations achieve high local concentrations of paclitaxel at the tumor site, wherein the invention formulations are substantially free of cremophor. Primary tumors contemplated for treatment with invention formulations include cancers of prostate, testes, lung, kidney, pancreas, bone, spleen, liver, brain, and the like.

In accordance with another embodiment of the present invention, there are provided pharmaceutically acceptable formulations of paclitaxel useful for the treatment of brain tumors in a subject, which formulations achieve high local concentrations of paclitaxel at the tumor site, and wherein said formulations are substantially free of cremophor, thereby inducing reduced cerebral and/or neurologic toxicity.

Invention formulations are useful for the treatment of a variety of indications, e.g., brain tumors, intraperitoneal tumors, prostatitis, bph, restenosis, atherosclerosis, and the like. Invention compositions have been observed to reduce the rate of metabolism of paclitaxel (relative to the rate of metabolism when paclitaxel is formulated for delivery as described in the prior art, e.g., as Taxol), thus a higher activity remains 24 hrs after administration.

In accordance with yet another embodiment of the present invention, there are provided pharmaceutically acceptable formulations of paclitaxel useful for the reduction of serum testosterone levels (low dose paclitaxel) in a subject. Such formulations are useful for the treatment of various urogenital disorders.

Paclitaxel-containing formulations according to the invention can be lyophilized, and conveniently reconstituted at concentrations greater than about 1.2 mg/ml (with concentrations greater than about 2 mg/ml preferred, and concentrations greater than about 3 mg/ml being especially preferred). The resulting reconstituted materials are stable for at least 3 days. Another advantage of paclitaxel-containing formulations according to the invention is their suitability for administration using standard i.v. infusion tubing (i.e., there is no need to use specialized tubing to delivery paclitaxel).

Paclitaxel-containing formulations according to the invention can be administered employing relatively small volumes for delivery, e.g., typically requiring infusion volumes <200 ml for a therapeutic dose. In addition, infusion can typically be accomplished over a relatively short period of time, e.g., over about 2–3 hrs, delivering doses >about 250–300 $mg/m^2$.

Because invention formulations can be delivered in substantially higher concentrations than heretofor available in the art, and over substantially reduced time periods, use of invention formulations frequently eliminates the necessity for a patient to remain under direct medical observation for extended periods of time.

In accordance with yet another embodiment of the present invention, there are provided methods for the administration of paclitaxel to a subject in need thereof, said methods comprising systemically administering a therapeutically effective amount of paclitaxel to said subject in a pharmaceutically acceptable formulation without the use of premedication, wherein said paclitaxel can optionally be administered as a bolus injection.

As readily recognized by those of skill in the art, invention compositions can be administered over a variety of time-frames. Of course it is recognized that the more quickly a medicament can be delivered to a patient, the less intrusive the procedure will be. Accordingly, it is presently preferred that the administration period is no greater than about 1 hour, and that the treatment cycle last no greater than about 2 weeks.

Suitable therapeutically effective doses can readily be determined by those of skill in the art, typically falling in the range of about 135 mg/m$^2$, with doses of at least about 175 mg/m$^2$ being presently preferred and doses of at least about 200 mg/m$^2$ being especially preferred.

In accordance with a particularly preferred aspect of the present invention, there are provided methods for reducing the hematologic toxicity of paclitaxel in a subject undergoing treatment therewith, said methods comprising systemically administering paclitaxel to said subject in a pharmaceutically acceptable formulation, as described herein. Preferably, such formulations are substantially free of cremophor.

In accordance with another particularly preferred aspect of the present invention, there are provided methods for reducing the cerebral or neurologic toxicity of paclitaxel in a subject undergoing treatment therewith, said methods comprising systemically administering said paclitaxel to said subject in a pharmaceutically acceptable formulation as described herein. Preferably, such formulations are substantially free of cremophor.

In accordance with yet another particularly preferred aspect of the present invention, there are provided methods for the treatment of primary tumors in a subject by achieving high local concentration of paclitaxel at the tumor site, said methods comprising systemically administering paclitaxel to said subject in a pharmaceutically acceptable formulation free of cremophor. Primary tumors contemplated for treatment by invention methods include cancers of prostate, testes, lung, kidney, pancreas, bone, spleen, liver, brain, and the like.

In accordance with still another embodiment of the present invention, there are provided unit dosage forms comprising a vessel containing a sufficient quantity of paclitaxel to allow systemic administration at a dose of at least 135 mg/m$^2$ over an administration period of no greater than 2 hours. As readily recognized by those of skill in the art, paclitaxel used for the preparation of such unit dosage forms can be in aqueous media, a non-aqueous formulation of paclitaxel, a dry powder formulation of paclitaxel, and the like.

The invention will now be described in greater detail by reference to the following non-limiting examples.

Example 1

Preparation of Protein Shell Containing Oil

Three ml of a USP (United States Pharmacopoeia) 5% human serum albumin solution (Alpha Therapeutic Corporation) were taken in a cylindrical vessel that could be attached to a sonicating probe (Heat Systems, Model XL2020). The albumin solution was overlayed with 6.5 ml of USP grade soybean oil (soya oil). The tip of the sonicator probe was brought to the interface between the two solutions and the assembly was maintained in a cooling bath at 20° C. The system was allowed to equilibrate and the sonicator turned on for 30 seconds. Vigorous mixing occurred and a white milky suspension was obtained. The suspension was diluted 1:5 with normal saline. A particle counter (Particle Data Systems, Elzone, Model 280 PC) was utilized to determine size distribution and concentration of oil-containing protein shells. The resulting protein shells were determined to have a maximum cross-sectional dimension of about 1.35±0.73 microns, and the total concentration determined to be ~10$^9$ shells/ml in the original suspension.

As a control, the above components, absent the protein, did not form a stable microemulsion when subjected to ultrasonic irradiation. This result suggests that the protein is essential for formation of microspheres. This is confirmed by scanning electron micrograph and transmission electron micrograph studies as described below.

Example 2

Preparation of Polymeric Shells Containing Dissolved Taxol

Taxol was dissolved in USP grade soybean oil at a concentration of 2 mg/ml. 3 ml of a USP 5% human serum albumin solution was taken in a cylindrical vessel that could be attached to a sonicating probe. The albumin solution was overlayed with 6.5 ml of soybean oil/taxol solution. The tip of the sonicator probe was brought to the interface between the two solutions and the assembly was maintained in equilibrium and the sonicator turned on for 30 seconds. Vigorous mixing occurred and a stable white milky suspension was obtained which contained protein-walled polymeric shells enclosing the oil/taxol solution.

In order to obtain a higher loading of drug into the crosslinked protein shell, a mutual solvent for the oil and the drug (in which the drug has a considerably higher solubility) can be mixed with the oil. Provided this solvent is relatively non-toxic (e.g., ethyl acetate), it may be injected along with the original carrier. In other cases, it may be removed by evaporation of the liquid under vacuum following preparation of the polymeric shells.

It is recognized that several different methods may be employed to achieve the physical characteristics of the Capxol formulation. The biological properties associated with this formulation of higher local concentrations at specific organ sites (prostate, lung, pancreas, bone, kidney, heart) as well as lower toxicities (increased LD50, decreased myelosuppression, decreased cerebral toxicity) associated with higher efficacies is independent of the method of manufacture.

Example 3

In Vivo Biodistribution—Crosslinked Protein Shells Containing a Fluorophore

To determine the uptake and biodistribution of liquid entrapped within protein polymeric shells after intravenous injection, a fluorescent dye (rubrene, available from Aldrich) was entrapped within a human serum albumin (HSA) protein polymeric shell and used as a marker. Thus, rubrene was dissolved in toluene, and albumin shells containing toluene/rubrene were prepared as described above by ultrasonic irradiation. The resulting milky suspension was diluted five times in normal saline. Two ml of the diluted suspension was then injected into the tail vein of a rat over 10 minutes. One animal was sacrificed an hour after injection and another 24 hours after injection.

100 micron frozen sections of lung, liver, kidney, spleen, and bone marrow were examined under a fluorescent microscope for the presence of polymeric shell-entrapped fluorescent dye or released dye. At one hour, the majority of the polymeric shells appeared to be intact (i.e., appearing as brightly fluorescing particles of about 1 micron diameter), and located in the lungs and liver. At 24 hours, the dye was observed in the liver, lungs, spleen, and bone marrow. A general straining of the tissue was also observed, indicating that the shell wall of the polymeric shells had been digested, and the dye liberated from within. This result was consistent with expectations and demonstrates the potential use of invention compositions for delayed or controlled release of an entrapped pharmaceutical agent such as taxol.

Example 4

Toxicity of Polymeric Shells Containing Soybean Oil (SBO)

Polymeric shells containing soybean oil were prepared as described in Example 1. The resulting suspension was diluted in normal saline to produce two different solutions, one containing 20% SBO and the other containing 30% SBO.

Intralipid, a commercially available TPN agent, contains 20% SBO. The $LD_{50}$ for Intralipid in mice is 120 ml/kg, or about 4 ml for a 30 g mouse, when injected at 1 cc/min.

Two groups of mice (three mice in each group; each mouse weighing about 30 g) were treated with invention composition containing SBO as follows. Each mouse was injected with 4 ml of the prepared suspension of SBO-containing polymeric shells. Each member of one group received the suspension containing 20% SBO, while each member of the other group received the suspension containing 30% SBO.

All three mice in the group receiving the suspension containing 20% SBO survived such treatment, and showed no gross toxicity in any tissues or organs when observed one week after SBO treatment. Only one of the three mice in the group receiving suspension containing 30% SBO died after injection. These results clearly demonstrate that oil contained within polymeric shells according to the present invention in not toxic at its $LD_{50}$ dose, as compared to a commercially available SBO formulation (Intralipid). This effect can be attributed to the slow release (i.e., controlled rate of becoming bioavailable) of the oil from within the polymeric shell. Such slow release prevents the attainment of a lethal dose of oil, in contrast to the high oil dosages attained with commercially available emulsions.

Example 5

In vivo Bioavailability of Soybean Oil Released from Polymeric Shells

A test was performed to determine the slow or sustained release of polymeric shell-enclosed material following the injection of a suspension of polymeric shells into the blood stream of rats. Crosslinked protein (albumin) walled polymeric shells containing soybean oil (SBO) were prepared by sonication as described above. The resulting suspension of oil-containing polymeric shells was diluted in saline to a final suspension containing 20% oil. Five ml of this suspension was injected into the cannulated external jugular vein of rats over a 10 minute period. Blood was collected from these rats at several time points following the injection and the level of triglycerides (soybean oil is predominantly triglyceride) in the blood determined by routine analysis.

Five ml of a commercially available fat emulsion (Intralipid, an aqueous parenteral nutrition agent—containing 20% soybean oil, 1.2% egg yolk phospholipids, and 2.25% glycerin) was used as a control. The control utilizes egg phosphatide as an emulsifier to stabilize the emulsion. A comparison of serum levels of the triglycerides in the two cases would give a direct comparison of the bioavailability of the oil as a function of time. In addition to the suspension of polymeric shells containing 20% oil, five ml of a sample of oil-containing polymeric shells in saline at a final concentration of 30% oil was also injected. Two rats were used in each of the three groups. The blood levels of triglycerides in each case are tabulated in Table 1, given in units of mg/dl.

TABLE 1

| | SERUM TRIGLYCERIDES (mg/dl) | | | | | |
|---|---|---|---|---|---|---|
| GROUP | Pre | 1 hr | 4 hr | 24 hr | 48 hr | 72 hr |
| Intralipid Control (20% SBO) | 11.4 | 941.9 | 382.9 | 15.0 | 8.8 | 23.8 |
| Polymeric Shells (20% SBO) | 24.8 | 46.7 | 43.8 | 29.3 | 24.2 | 43.4 |
| Polymeric Shells (30% SBO) | 33.4 | 56.1 | 134.5 | 83.2 | 34.3 | 33.9 |

Blood levels before injection are shown in the column marked 'Pre'. Clearly, for the Intralipid control, very high triglyceride levels are seen following injection. Triglyceride levels are then seen to take about 24 hours to come down to preinjection levels. Thus the oil is seen to be immediately available for metabolism following injection.

The suspension of oil-containing polymeric shells containing the same amount of total oil as Intralipid (20%) show a dramatically different availability of detectible triglyceride in the serum. The level rises to about twice its normal value and is maintained at this level for many hours, indicating a slow or sustained release of triglyceride into the blood at levels fairly close to normal. The group receiving oil-containing polymeric shells having 30% oil shows a higher level of triglycerides (concomitant with the higher administered dose) that falls to normal within 48 hours. Once again, the blood levels of triglyceride do not rise astronomically in this group, compared to the control group receiving Intralipid. This again, indicates the slow and sustained availability of the oil from invention composition, which has the advantages of avoiding dangerously high blood levels of material contained within the polymeric shells and availability over an extended period at acceptable levels. Clearly, drugs delivered within polymeric shells of the present invention would achieve these same advantages.

Such a system of soybean oil-containing polymeric shells could be suspended in an aqueous solution of amino acids, essential electrolytes, vitamins, and sugars to form a total parenteral nutrition (TPN) agent. Such a TPN cannot be formulated from currently available fat emulsions (e.g., Intralipid) due to the instability of the emulsion in the presence of electrolytes.

Example 6

Preparation of Protein-walled Polymeric Shells Containing a Solid Core of Pharmaceutically Active Agent Another method of delivering a poorly water-soluble drug such as taxol within a polymeric shell is to prepare a shell of polymeric material around a solid drug core. Such a 'protein coated' drug particle may be obtained as follows. The procedure described in Example 2 is repeated using an organic solvent to dissolve taxol at a relatively high concentration. Solvents generally used are organics such as benzene, toluene, hexane, ethyl ether, chloroform, alcohol and the like. Polymeric shells are produced as described in Example 1. Five ml of the milky suspension of polymeric shells containing dissolved taxol are diluted to 10 ml in normal saline. This suspension is placed in a rotary and the volatile organic removed by vacuum. The resultant suspension is examined under a microscope to reveal opaque cores, indicating removal of substantially all organic solvent, and the presence of solid taxol. The suspension can be frozen and stored indefinitely and used directly or lyophilized at a later time.

Alternatively, the polymeric shells with cores of organic solvent-containing dissolved drug are freeze-dried to obtain a dry crumbly powder that can be resuspended in saline (or other suitable liquid) at the time of use. Although the presently preferred protein for use in the formation of the polymeric shell is albumin, other proteins such as a-2-macroglobulin, a known opsonin, could be used to enhance uptake of the polymeric shells by macrophage-like cells. Alternatively, molecules like PEG could be incorporated into the particles to produce a polymeric shell with increased circulation time in vivo.

Example 7

Targeting of Immunosuppressive Agent to Transplanted Organs Using Intravenous Delivery of Polymeric Shells Containing Such Agents Immunosuppressive agents are extensively used following organ transplantation for the prevention of rejection episodes. In particular, cyclosporine, a potent immunosuppressive agent, prolongs the survival of allogeneic transplants involving skin, heart, kidney, pancreas, bone marrow, small intestine, and lung in animals. Cyclosporine has been demonstrated to suppress some humoral immunity and to a greater extent, cell mediated reactions such as allograft rejection, delayed hypersensitivity, experimental allergic encephalomyelitis, Freund's adjuvant arthritis, and graft versus host disease in many animal species for a variety of organs. Successful kidney, liver and heart allogeneic transplants have been performed in humans using cyclosporine.

Cyclosporine is currently delivered in oral form either as capsules containing a solution of cyclosporine in alcohol, and oils such as corn oil, polyoxyethylated glycerides and the like, or as a solution in olive oil, polyoxyethylated glycerides, and the like. It is also administered by intravenous injection, in which case it is dissolved in a solution of ethanol (approximately 30%) and Cremaphor (polyoxyethylated castor oil) which must be diluted 1:20 to 1:100 in normal saline or 5% dextrose prior to injection. Compared to an intravenous (i.v.) infusion, the absolute bioavailability of the oral solution is approximately 30% (Sandoz Pharmaceutical Corporation, Publication SDI-Z10 (A4), 1990). In general, the i.v. delivery of cyclosporine suffers from similar problems as the currently practiced i.v. delivery of taxol, i.e., anaphylactic and allergic reactions believed to be due to the Cremaphor, the delivery vehicle employed for the i.v. formulation. In addition, the intravenous delivery of drug (e.g., cyclosporine) encapsulated as described here avoids dangerous peak blood levels immediately following administration of drug. For example, a comparison of currently available formulations for cyclosporine with the above-described encapsulated form of cyclosporine showed a five-fold decrease in peak blood levels of cyclosporine immediately following injection.

In order to avoid problems associated with the Cremaphor, cyclosporine contained within polymeric shells as described above may be delivered by i.v. injection. It may be dissolved in a biocompatible oil or a number of other solvents following which it may be dispersed into polymeric shells by sonication as described above. In addition, an important advantage to delivery cyclosporine (or other immunosuppressive agent) in polymeric shells has the advantage of local targeting due to uptake of the injected material by the RES system in the liver. This may, to some extent, avoid systemic toxicity and reduce effective dosages due to local targeting.

Example 8

Antibody Targeting of Polymeric Shells

The nature of the polymeric shells of the invention allows for the attachment of monoclonal or polyclonal antibodies to the polymeric shell, or the incorporation of antibodies into the polymeric shell. Antibodies can be incorporated into the polymeric shell as the polymeric microcapsule shell is being formed, or antibodies can be attached to the polymeric shell after preparation thereof. Standard protein immobilization techniques can be used for this purpose. For example, with protein microcapsules prepared from a protein such as albumin, a large number of amino groups on the albumin lysine residues are available for attachment of suitably modified antibodies. As an example, antitumor agents can be delivered to a tumor by incorporating antibodies against the tumor into the polymeric shell as it is being formed, or antibodies against the tumor can be attached to the polymeric shell after preparation thereof. As another example, gene products can be delivered to specific cells (e.g., hepatocytes or certain stem cells in the bone marrow) by incorporating antibodies against receptors on the target cells into the polymeric shell as it is being formed, or antibodies against receptors on the target cells can be attached to the polymeric shell after preparation thereof. In addition, monoclonal antibodies against nuclear receptors can be used to target the encapsulated product to the nucleus of certain cell types.

Example 9

Polymeric Shells as Carriers for Polynucleotide Constructs, Enzymes and Vaccines As gene therapy becomes more widely accepted as a viable therapeutic option (at the present time, over 40 human gene transfer proposals have been approved by NIH and/or FDA review boards), one of the barriers to overcome in implementing this therapeutic approach is the reluctance to use viral vectors for the incorporation of genetic material into the genome of a human cell. Viruses are inherently toxic. Thus, the risks entailed in the use of viral vectors in gene therapy, especially for the treatment of non-lethal, non-genetic diseases, are unacceptable. Unfortunately, plasmids transferred without the use of a viral vector are usually not incorporated into the genome of the target cell. In addition, as with conventional drugs, such plasmids have a finite half life in the body. Thus, a general limitation to the implementation of gene therapy (as well as antisense therapy, which is a reverse form of gene therapy, where a nucleic acid or oligonucleotide is introduced to inhibit gene expression) has been the inability to effectively deliver nucleic acids or oligonucleotides which are too large to permeate the cell membrane.

The encapsulation of DNA, RNA, plasmids, oligonucleotides, enzymes, and the like, into protein microcapsule shells as described herein can facilitate their targeted delivery to the liver, lung, spleen, lymph and bone marrow. Thus, in accordance with the present invention, such biologics can be delivered to intracellular locations without the attendant risk associated with the use of viral vectors. This type of formulation facilitates the non-specific uptake or endocytosis of the polymeric shells directly from the blood stream to the cells of the RES, into muscle cells by intramuscular injection, or by direct injection into tumors. In addition, monoclonal antibodies against nuclear receptors can be used to target the encapsulated product to the nucleus of certain cell types.

Diseases that can be targeted by such constructs include diabetes, hepatitis, hemophilia, cystic fibrosis, multiple sclerosis, cancers in general, flu, AIDS, and the like. For example, the gene for insulin-like growth factor (IGF-1) can be encapsulated into protein shells for delivery for the treatment of diabetic peripheral neuropathy and cachexia. Genes encoding Factor IX and Factor VIII (useful for the treatment of hemophilia) can be targeted to the liver by encapsulation into protein microcapsule shells of the present invention. Similarly, the gene for the low density lipoprotein (LDL) receptor can be targeted to the liver for treatment of atherosclerosis by encapsulation into protein microcapsule shells of the present invention.

Other genes useful in the practice of the present invention are genes which re-stimulate the body's immune response against cancer cells. For example, antigens such as HLA-B7, encoded by DNA contained in a plasmid, can be incorporated into a protein shell of the present invention for injection directly into a tumor (such as a skin cancer). Once in the tumor, the antigen will recruit to the tumor specific cells which elevate the level of cytokines (e.g., IL-2) that render the tumor a target for immune system attack.

As another example, plasmids containing portions of the adeno-associated virus genome are contemplated for encapsulation into protein microcapsule shells of the present invention. In addition, protein microcapsule shells of the present invention can be used to deliver therapeutic genes to CD8+ T cells, for adoptive immunotherapy against a variety of tumors and infectious diseases.

Protein shells of the present invention can also be used as a delivery system to fight infectious diseases via the targeted delivery of an antisense nucleotide, for example, against the hepatitis B virus. An example of such an antisense oligonucleotide is a 21-mer phosphorothioate against the polyadenylation signal of the hepatitis B virus.

Protein shells of the present invention can also be used for the delivery of the cystic fibrosis transmembrane regulator (CFTR) gene. Humans lacking this gene develop cystic fibrosis, which can be treated by nebulizing protein microcapsule shells of the present invention containing the CFTR gene, and inhaling directly into the lungs.

Enzymes can also be delivered using the protein shells of the present invention. For example, the enzyme, DNAse, can be encapsulated and delivered to the lung. Similarly, ribozymes can be encapsulated and targeted to virus envelop proteins or virus infected cells by attaching suitable antibodies to the exterior of the polymeric shell. Vaccines can also be encapsulated into polymeric microcapsules of the present invention and used for subcutaneous, intramuscular or intravenous delivery.

Example 10

Localized Treatment of Brain Tumors and Tumors Within the Peritoneum

Delivering chemotherapeutic agents locally to a tumor is an effective method for long term exposure to the drug while minimizing dose limiting side effects. The biocompatible materials discussed above may also be employed in several physical forms such as gels, crosslinked or uncrosslinked to provide matrices from which the pharmacologically active ingredient, for example paclitaxel, may be released by diffusion and/or degradation of the matrix. Capxol may be dispersed within a matrix of the biocompatible material to provide a sustained release formulation of paclitaxel for the treatment of brain tumors and tumors within the peritoneal cavity (ovarian cancer and metastatic diseases). Temperature sensitive materials may also be utilized as the dispersing matrix for the invention formulation. Thus for example, the Capxol may be injected in a liquid formulation of the temperature sensitive materials (e.g., copolymers of polyacrylamides or copolymers of polyalkylene glycols and polylactide/glycolides and the like) which gel at the tumor site and provide slow release of Capxol. The Capxol formulation may be dispersed into a matrix of the above mentioned biocompatible polymers to provide a controlled release formulation of paclitaxel, which through the properties of the Capxol formulation (albumin associated with paclitaxel) results in lower toxicity to brain tissue as well as lower systemic toxicity as discussed below. This combination of Capxol or other chemotherapeutic agents formulated similar to Capxol together with a biocompatible polymer matrix may be useful for the controlled local delivery of chemotherapeutic agents for treating solid tumors in the brain and peritoneum (ovarian cancer) and in local applications to other solid tumors. These combination formulations are not limited to the use of paclitaxel and may be utilized with a wide variety of pharmacologically active ingredients including antiinfectives, immunosuppressives and other chemotherapeutics and the like.

Example 11

Stability of Capxol™ Following Reconstitution

Lyophilized Capxol in glass vials was reconstituted with sterile normal saline to concentrations of 1, 5, 10, and 15 mg/ml. and stored at room temperature and under refrigerated conditions. The suspensions was found to be homogeneous for at least three days under these conditions. Particle size measurements performed at several time points indicated no change in size distribution. No precipitation was seen under these conditions. This stability is unexpected and overcomes problems associated with Taxol, which precipitates in within about 24 hours after reconstitution at the recommended concentrations of 0.6–1.2 mg/ml.

In addition, reconstituted Capxol was stable in presence of different polymeric tubing materials such as teflon, silastic, polyethylene, tygon, and other standard infusion tubing materials. This is a major advantage over Taxol which is limited to polyethylene infusion sets and glass infusion bottles.

Example 12

Unit Dosage Forms for Capxol™

Capxol is prepared as a lyophilized powder in vials of suitable size. Thus a desired dosage can be filled in a suitable container ad lyophilized to obtain a powder containing essentially albumin and paclitaxel in the desired quantity. Such containers are then reconstituted with sterile normal saline or other aqueous diluent to the appropriate volume at the point of use to obtain a homogeneous suspension of paclitaxel in the diluent. This reconstituted solution can be directly administered to a patient either by injection or infusion with standard i.v. infusion sets.

Example 13

Study of Myelosuppression in Rats With Capxol™ and TAXOL® Following a Single Intravenous Administration Myelosuppression and other hemopoietic effects have been reported as adverse events after treatment with TAXOL. This study was designed to compare the effects of Capxol with TAXOL in rats after a single intravenous injection. The effects of both the Capxol and TAXOL carrier vehicles were also tested. Both Capxol and TAXOL were tested at a dose of 5 mg/kg paclitaxel while the carrier vehicle were tested individually at the respective concentrations used to suspend 5 mg/kg of paclitaxel. Therefore, 766 mg/kg of TAXOL vehicle and 50 mg/kg of Capxol vehicle was administered for these treatments. Changes in body weight and white blood cell counts were used to evaluate the hemopoietic effects.

Capxol produced significantly less (P<0.05) myelosuppression than TAXOL as determined by white cell counts at days 1 and 7 and a highly significant (P<0.01) reduction in white cell counts at day 10. Capxol also showed significantly less decreases in weight at days 1 and 10 than TAXOL. The TAXOL vehicle decreased WBCs for days 1 and 3 (P<0.01) when compared to the Capxol vehicle and also significantly decreased WBCs on day 1 when compared to Capxol (P<0.05). Significant decreases in body weights (P<0.05) were also observed for the TAXOL vehicle when compared to both Capxol and its vehicle. White cell counts were back to normal by day 7 for the Capxol treated animals but returned to normal only by day 14 for the TAXOL group. Results are presented in Table 2.

TABLE 2

| Group | Dose (mg/kg) | # of Animals (n) | Observation |
|---|---|---|---|
| Capxol | 5 | 4 | Significantly less myelosuppression and weight loss than with TAXOL |
| TAXOL | 5 | 4 | Significantly greater myelosuppression than Capxol |
| TAXOL Vehicle | 766 | 2 | Decrease in WBCs for day 1 and 3 compared to Capxol vehicle. Significant decrease in WBC on day 1 compared to Capxol |
| Capxol Vehicle | 50 | 2 | No effect on WBC count |

It is very surprising that when Capxol and Taxol are administered to rats at equivalent doses of paclitaxel, a much higher degree of myelosuppression results for the Taxol group compared to the Capxol group. This can result in lower incidences of infections and fever episodes (e.g., febrile neutropenia). It can also reduce the cycle time in between treatments which is currently 21 days. With the use of Capxol, this cycle time may be reduced to 2 weeks or less allowing for more effective treatment for cancers. Thus the use of Capxol may provide substantial advantage over Taxol.

Example 14

Determination of the $LD_{50}$ in Mice for Capxol™ and TAXOL® Following a Single Intravenous Administration The $LD_{50}$ of Capxol, TAXOL and their carrier vehicles was compared following a single intravenous administration. A total of 48 CD1 mice were used. Paclitaxel doses of 30, 103, 367, 548, and 822 mg/kg were tested for Capxol and doses of 4, 6, 9, 13.4, and 20.1 mg/kg paclitaxel for TAXOL. The dose for human albumin, the vehicle for Capxol, was only tested at 4.94 g/kg (corresponds to a dose of 548 mg/mL Capxol) because human albumin is not considered toxic to humans. The doses tested for the TAXOL vehicle (Cremophor EL®) were 1.5, 1.9, 2.8, and 3.4 mL/kg which correspond to doses of 9, 11.3, 16.6, and 20.1 mg/kg of paclitaxel, respectively. Three to four mice were dosed with each concentration.

The results indicated that paclitaxel administered in Capxol is less toxic than TAXOL or the TAXOL vehicle administered alone. The $LD_{50}$ and $LD_{10}$ for Capxol were 447.4 and 371.5 mg/kg of paclitaxel, 7.53 and 5.13 mg/kg of paclitaxel in TAXOL, and 1325 and 794 mg/kg of the TAXOL vehicle, (corresponds to a dose of 15.06 and 9.06 mg/kg TAXOL). In this study, the $LD_{50}$ for Capxol was 59 times greater than TAXOL and 29 times greater than the TAXOL vehicle alone. The $LD_{50}$ for paclitaxel in Capxol was 72 times greater than paclitaxel in TAXOL. Review of all the data in this study suggests that the TAXOL vehicle is responsible for much of the toxicity of TAXOL. It was seen that the mice receiving TAXOL and TAXOL vehicle showed classic signs of severe hypersensitivity indicated by bright pink skin coloration shortly after administration. No such reaction was seen for the Capxol and Capxol vehicle groups. Results are presented in Table 3.

TABLE 3

| | Single Intravenous Administration | | | | | |
|---|---|---|---|---|---|---|
| Group | Dose (mg/kg) | # of Animal | # of Deaths | % | $LD_{50}$ (mg/kg) | MTD or $LD_{10}$ |
| Capxol | 822 | 3 | 3 | 0 | 447.4 | 371.5 |
| | 548 | 4 | 4 | 0 | | |
| | 367 | 3 | 0 | 100 | | |
| | 103 | 3 | 0 | 100 | | |
| | 30 | 3 | 0 | 100 | | |
| TAXOL | 20.1 | 4 | 4 | 0 | 7.53 | 5.13 |
| | 13.4 | 4 | 4 | 0 | | |
| | 9 | 3 | 2 | 33 | | |
| | 6 | 4 | 1 | 75 | | |
| | 4 | 3 | 0 | 100 | | |

These high doses of Capxol were administered as bolus injections and represent the equivalent of approximately 80–2000 mg/m² dose in humans. The LD10 or maximum tolerated dose of Capxol in this study is equivalent to approximately 1000 mg/m² in humans. This is significantly higher than the approved human dose of 175 mg/m² for TAXOL.

To our surprise, it was found that the vehicle, Cremophor/Ethanol alone caused severe hypersensitivity reactions and death in several dose groups of mice. The LD50 data for the TAXOL vehicle alone shows that it is considerably more toxic than Capxol and significantly contributes to the toxicity of TAXOL. It has been unclear in the literature, the cause of hypersensitivity, however, based on these data, we believe that HSR's can be attributed to the Taxol vehicle.

Example 15

Determination of the $LD_{50}$ in Mice of Capxol™ and TAXOL® Following Multiple Intravenous Administrations The $LD_{50}$ of Capxol and TAXOL was compared following multiple intravenous administrations. A total of 32 CD1 mice were used. Capxol with paclitaxel doses of 30, 69, and 103 mg/kg were administered daily for five consecutive days. TAXOL with paclitaxel doses of 4, 6, 9, 13.4, and 20.1 mg/kg was administered daily for 5 consecutive days. Four mice were dosed with each concentration. Results are presented in Table 4.

TABLE 4

| | Multiple Intravenous Administrations | | | | | |
|---|---|---|---|---|---|---|
| Group | Dose (mg/kg) | # of Animal | # of Deaths | % | $LD_{50}$ (mg/kg | MTD or $LD_{10}$ |
| Capxol | 103 | 4 | 4 | 0 | 76. | 64. |
| | 69 | 4 | 1 | 75 | | |
| | 30 | 4 | 0 | 10 | | |
| TAXOL | 20.1 | 4 | 4 | 0 | 8.0 | 4.3 |
| | 13.4 | 4 | 4 | 0 | | |
| | 9 | 4 | 2 | 50 | | |
| | 6 | 4 | 1 | 75 | | |
| | 4 | 4 | 0 | 10 | | |

The results indicated that Capxol is less toxic than TAXOL. The $LD_{50}$ and $LD_{10}$ of Capxol were 76.2 and 64.5 mg/kg of paclitaxel, respectively, compared to 8.07 and 4.3 mg/kg of paclitaxel in TAXOL, respectively. In this study, the $LD_{50}$ for Capxol was 9.4 times higher than for TAXOL. The $LD_{10}$ for Capxol was 15 times higher for Capxol than for TAXOL. The results of this study suggests that the Capxol is less toxic than TAXOL when administered in multiple doses at daily intervals.

Example 16

Toxicity and Efficacy of Two Formulation of Capxol and TAXOL

A study was performed to determine the efficacy of Capxol, TAXOL, and the Capxol vehicle in female athymic NCr-nu mice implanted with MX-1 human mammary tumor fragments.

Groups of 5 mice each were given intravenous injections of Capxol formulation VR-3 or VR-4 at doses of 13.4, 20, 30, 45 mg/kg/day for 5 days. Groups of 5 mice were also each given intravenous injections of TAXOL at doses of 13.4, 20 and 30 mg/kg/day for five days. A control group of ten mice was treated with an intravenous injection of Capxol vehicle control (Human Albumin, 600 mg/kg/day) for 5 days. Evaluation parameters were the number of complete tumor regressions, the mean duration of complete regression, tumor-free survivors, and tumor recurrences.

Treatment with Capxol formulation VR-3 resulted in complete tumor regressions at all dose levels. The two highest doses resulted in 100% survival after 103 days. Capxol formulation VR-4 resulted in complete tumor regression in the three highest dose groups, and 60% regressions at 13.4 mg/kg/day. Survival rates after 103 days were somewhat less than with formulation VR-4. Treatment with TAXOL at 30, 20, and 13.4 mg/kg/day resulted in 103 day survival rates of 40%, 20%, and 20% respectively. Treatment with the control vehicle had no effect on tumor growth and the animals were sacrificed after 33 to 47 days. Results are presented in Table 5.

TABLE 5

| Dosage | CR/Total | | | TSF/TR | | | DCR (days) | | | Non Specific Deaths/Total | | |
|---|---|---|---|---|---|---|---|---|---|---|---|---|
| (mg/kg/day) | VR-3 | VR-4 | TAX | VR-3 | VR-4 | TAX | VR-3 | VR-4 | TAX | VR-3 | VR-4 | TAX |
| 45 | 5/5 | 5/5 | NA | 5/0 | 3/2 | NA | >88 | >73 | NA | 0/5 | 0/5 | NA |
| 30 | 5/5 | 5/5 | 4/4 | 5/0 | 5/0 | 2/2 | >88 | >88 | >56 | 0/5 | 0/5 | 1/5 |
| 20 | 5/5 | 5/5 | 4/4 | 1/4 | 2/3 | 1/3 | >51 | >47 | >57 | 0/5 | 0/5 | 1/5 |
| 13.4 | 4/5 | 3/5 | 4/5 | 0/5 | 0/5 | 1/4 | 10 | 8 | >29 | 0/5 | 0/5 | 0/5 |

CR = Complete tumor regression;
TFS = Tumor free survivor;
TR = Tumor recurrence;
DCR = days of complete regression These unexpected and surprising results show an increased efficacy for the two capxol formulation compared to TAXOL. In addition, higher doses of paclitaxel are achieved in the Capxol groups due to lower toxicity of the formulation. These high doses were administered as bolus injections.

Example 17

Blood Kinetics and Tissue Distribution on $^3$H-TAXOL™ and Capxol™ Following a Single Intravenous Dose in the Rat Two studies were performed to compare the pharmacokinetics and tissue distribution of $^3$H-paclitaxel formulated in Capxol and TAXOL Injection Concentrate. Fourteen male rats were intravenously injected with 10 mg/kg of $^3$H-TAXOL and 10 rats with 4.9 mg/kg. Ten male rats were intravenously injected with 5.1 mg/kg $^3$H-Capxol in the above study.

Levels of both total radioactivity and paclitaxel decline bi-phasically in blood of rats following 5 mg/kg IV bolus doses of either $^3$H-TAXOL or $^3$H-Capxol. However, the levels of both total radioactivity and paclitaxel are significantly lower following administration of $^3$H-Capxol following a similar $^3$H-TAXOL dose. This lower level is more rapidly distributed out of the blood.

The blood HPLC profile shows a similar pattern of metabolism to highly polar metabolite(s) for both $^3$H Capxol and $^3$H-TAXOL. However, the rate of metabolism appears significantly slower for $^3$H-Capxol as 44.2% of blood radioactivity remains as paclitaxel 24 hours post-dose versus 27.7% for $^3$H-TAXOL. The excretion of radioactivity occurs only minimally in the urine and predominantly in the feces for $^3$H-Capxol which is similar to reported excretion patterns for $^3$H-TAXOL. The blood kinetics for total radioactivity and paclitaxel following IV administration of $^3$H-Capxol or $^3$H-TAXOL at 5 mg/kg are presented in Table 6.

TABLE 6

| Treatment | AUC$_{0-24}$ (µg eq.hr/mL) | Extrapolated C$_0$ (µg eq/mL) | Observed C$_{max}$ (µg eq/(mL) | Observed T$_{max}$ (hr) | t½β (hr) |
|---|---|---|---|---|---|
| Total Radioactivity | 6.1 | 7.6 | 4.2 | 0.03 | 19.0 |
| $^3$H-Capxol | 10.2 | 19.7 | 13.5 | 0.03 | 19.7 |
| $^3$H-TAXOL | | | | | |
| Paclitaxel | 3.7 | 7.0 | 4.0 | 0.03 | 11.4 |
| 3H-Capxol | 5.4 | 17.1 | 11.8 | 0.03 | |
| 3H-TAXOL | | | | | 7.2 |

The tissue radioactivity levels are higher following $^3$H-Capxol administration than $^3$H-TAXOL administration for 12 of 14 tissues. The tissue/blood ppm ratios are higher in all tissues for $^3$H-Capxol dosed animals as the blood levels are lower. This supports the rapid distribution of $^3$H-Capxol from the blood to the tissues suggested by the blood kinetic data.

$^3$H-Paclitaxel formulated in Capxol shows a similar pharmacokinetic profile to $^3$H-paclitaxel formulated in TAXOL for Injection concentrate, but tissue/blood ppm ratios and metabolism rates differ significantly. A significantly lower level of total radioactivity for Capxol treated animals than for TAXOL treated animals in the 2 minute post administration blood sample indicates that the $^3$H-Capxol is more rapidly distributed out of the blood. However, the rate of metabolism appears significantly slower for $^3$H-Capxol as 44% of blood reactivity remains as paclitaxel at 24 hours post-administration versus 28% for $^3$H-TAXOL.

This finding for Capxol is surprising and provides a novel formulation to achieve sustained activity of paclitaxel compared to TAXOL. Taken together with local high concentrations, this enhanced activity should result in increased efficacy for the treatment of primary tumors or metastases in organs with high local concentrations.

Tissue distributions are presented in Table 7 below. The data represent the mean and standard deviations of 10 rats in each group (Capxol and TAXOL).

TABLE 7

Radioactive Residues in Tissues of Male Rats, Expressed as ppm following a single intravenous dose of $^3$H-Capxol and $^3$H-Taxol at 5 mg/kg

| Sample | Capxol Mean ± SD Values | | Taxol Mean ± SD Values | |
|---|---|---|---|---|
| Brain | 0.106 | 0.008 | 0.145 | 0.020 |
| Heart | 0.368 | 0.063 | 0.262 | 0.037 |

TABLE 7-continued

Radioactive Residues in Tissues of Male Rats, Expressed as ppm following a single intravenous dose of $^3$H-Capxol and $^3$H-Taxol at 5 mg/kg

| Sample | Capxol Mean ± SD Values | | Taxol Mean ± SD Values | |
|---|---|---|---|---|
| Lung | 1.006 | 0.140 | 0.694 | 0.057 |
| Liver | 1.192 | 0.128 | 1.37 | 0.204 |
| Kidney | 0.670 | 0.110 | 0.473 | 0.068 |
| Muscle | 0.422 | 0.120 | 0.386 | 0.035 |
| GI Tract | 0.802 | 0.274 | 0.898 | 0.243 |
| Testes | 0.265 | 0.023 | 0.326 | 0.047 |
| Pancreas | 0.963 | 0.357 | 0.468 | 0.070 |
| Carcass | 0.596 | 0.070 | 0.441 | 0.065 |
| Bone | 0.531 | 0.108 | 0.297 | 0.051 |
| Spleen | 0.912 | 0.131 | 0.493 | 0.070 |
| Prostate | 1.728 | 0.356 | 1.10 | 0.161 |
| Seminal Vesicles | 1.142 | 0.253 | 1.20 | 0.237 |
| Blood | 0.131 | 0.010 | 0.181 | 0.020 |
| Plasma | 0.131 | 0.012 | 0.196 | 0.026 |

The data show significantly higher levels of accumulation of Capxol in the several organs when compared to Taxol. These organs include prostate, pancreas, kidney, lung, heart, bone, and spleen. Thus Capxol may be more effective than Taxol in the treatment of cancers of these organs at equivalent levels of paclitaxel.

Levels in the prostate tissue are of particular interest in the treatment of prostatic cancer. This surprising and unexpected result has implications for the treatment of prostate cancer. Table 8 below shows the data for individual rats (10 in each group) showing increased accumulation of paclitaxel in the prostate for Capxol as compared to TAXOL. The basis for the localization within the prostate could be a result of the particle size of the formulation (20–400 nm), or the presence the protein albumin in the formulation which may cause localization into the prostatic tissue through specific membrane receptors (gp 60, gp 18, gp 13 and the like). It is also likely that other biocompatible, biodegradable polymers other than albumin may show specificity to certain tissues such as the prostate resulting in high local concentration of paclitaxel in these tissues as a result of the properties described above. Such biocompatible materials are contemplated within the scope of this invention. A preferred embodiment of a composition to achieve high local concentrations of paclitaxel in the prostate is a formulation containing paclitaxel and albumin with a particle size in the range of 20–400 nm, and free of cremophor. This embodiment has also been demonstrated to result in higher level concentrations of paclitaxel in the, pancreas, kidney, lung, heart, bone, and spleen when compared to Taxol at equivalent doses.

TABLE 8

Data for 10 rats in each group
Dose 5 mg/kg paclitaxel

| CAPXOL ™ | BMS TAXOL ™ |
|---|---|
| 1.228 | 1.13 |
| 2.463 | 1.04 |
| 1.904 | 0.952 |
| 1.850 | 1.42 |
| 1.660 | 1.31 |
| 1.246 | 1.08 |

TABLE 8-continued

Data for 10 rats in each group
Dose 5 mg/kg paclitaxel

| CAPXOL ™ | BMS TAXOL ™ |
|---|---|
| 1.895 | 1.03 |
| 1.563 | 0.95 |
| 1.798 | 0.94 |
| 1.676 | 1.18 |
| Mean | Mean |
| SD | SD |

This unexpected localization of paclitaxel to the prostate in the Capxol formulation may be exploited for the delivery of other pharmacologically active agents to the prostate for the treatment of other disease states affecting that organ, e.g., antibiotics in a similar formulation for the treatment of prostatitis (inflammation and infection of the prostate), therapeutic agents effective for the treatment of benign prostatic hypertrophy maybe formulated in a similar fashion to achieve high local delivery. Similarly, the surprising finding that Capxol provides high local concentrations to the heart can be exploited for the treatment of restenosis as well as atherosclerotic disease in coronary vessels. Paclitaxel has been demonstrated to have a therapeutic effect in the prevention of restentosis and atherosclerosis and Capxol thus is an ideal vehicle. Furthermore it has been demonstrated that polymerized albumin preferentially binds to inflamed endothelial vessels possibly through gp60, gp18 and gp13 receptors.

Example 18

Blood Kinetics and Tissue Distribution of Paclitaxel Following Multiple Intravenous Dose Levels of Capxol™ in the Rat The study using $^3$H-Capxol was supplemented by treating four additional groups of rats with a single bolus dose of 9.1 mg/kg, 26.4 mg/kg, 116.7 mg/kg, and 148.1 mg/kg of paclitaxel in Capxol. Blood was collected from the tail vein and the $AUC_{0-24}$ was calculated. At 24 hours, blood samples were collected, extracted, and the extract injected on HPLC to determine the level of parent compound in the blood.

The blood kinetics for total radioactivity and paclitaxel following IV administration of $^3$H-Capxol are presented in Table 9.

TABLE 9

| Group/Dose (mg/kg) | $AUC_{0-24}$ (µg eq.hr/mL) | Extrapolated $C_0$ (µg eq/mL) | Observed $C_{max}$ (µg eq/(mL) | Observed $T_{max}$ (hr) | $t_{½}\beta$ (hr) |
|---|---|---|---|---|---|
| A/9.1 | 11.5 | 10.2 | 7.19 | 0.03 | 22.3 |
| B/26.4 | 43.5 | 44.8 | 29.5 | 0.03 | 16.0 |
| C/116.7 | 248.9 | 644.6 | 283.3 | 0.03 | 8.48 |
| D/148.1 | 355.3 | 1009.8 | 414.2 | 0.03 | 9.34 |

As the dose of paclitaxel was increased, the area under the curve was proportionally increased. The level of parent compound after 24 hours was increased by a factor of 8.5 (0.04 ppm–0.34 ppm), going from the 9 mg/kg dose to the 148 mg/kg dose.

Example 19

Determination of the Toxicity in Rats of Capxol™ and TAXOL Following a Single Intravenous Administration The objective of the study was to determine the toxicity of Capxol™ following a single IV administration in male and female rats. Capxol™ was administered to 6 male and 6 female rats at doses of 5, 9, 30, 90 and 120 mg/kg. One half of the animals from each dose group were euthanized and necropsied on Day 8. The remaining animals were necropsied on Day 31. The results of Capxol™-treated animals were compared to the results of normal saline and vehicle control groups as well as to the results of animals treated with 5, 9 and 30 mg/kg TAXOL.

Animals were examined immediately after dosing, 1 hour and 4 hours past administration and once daily thereafter. Blood was collected from each animal for hematological and serum determination prior to euthanasia.

Thirteen deaths occurred during the 30 day observation period. All 12 animals treated with TAXOL at a dose of 30 mg/kg paclitaxel died by day 4. Only one animal treated with Capxol died. The Capxol treated animal received 90 mg/kg paclitaxel and was found dead on day 15. No other animals treated with Capxol died at the 90 kg or 120 mg/kg dose, therefore the death is not thought to be treatment related.

During the first four hours observation period, piloerection and staggering gait were observed in the majority of animals treated with TAXOL, possibly due to the alcohol content of the drug. Piloerection was noted in a few animals treated with Capxol. Animals treated with TAXOL at a dose of 30 mg/kg paclitaxel were observed with piloerection and lethargy and were found dead by day 4. No overt signs of toxicity were observed in Capxol treated animals, except for a few incidences of piloerection at the 90 mg/mL and 120 mg/mL dose levels.

No abnormalities were reported in Capxol treated animals. Gross necropsy results for day 8 and day 31 were normal. Significant dose related changes were seen in the male reproductive organs in animals treated with Capxol. A degeneration and vacuolation of epididymal ductal epithelial cells, often accompanied by multifocal interstitial lymphocytic infiltrate, was observed. There was increasing severe atrophy of seminiferous tubules seen in the testes as the dose of Capxol increased. In the pathologist's opinion, there were significant lesions observed in the male reproductive organs of the animals treated with 9, 30, 90, and 120 mg/kg Capxol. These changes involved diffuse degeneration and necrosis of the testes. These changes were the most prevalent in animals that received higher doses of Capxol. No changes were seen in the testes from untreated control animals, vehicle control animals, or those treated with TAXOL.

This finding is unexpected and has significant therapeutic implications for the treatment of hormone dependent cancers such as prostate cancer. Removal of the testes (orchiectomy) is a therapeutic approach to the treatment of prostate cancer. Capxol represents a novel formulation for the treatment of this disease by achieving high local concentration of paclitaxel at that site, by sustained activity of the active ingredient, by reduction of testicular function and without the toxic cremophor vehicle. Treatment with Capxol thus allows for reduction in levels of testosterone and other androgen hormones.

Cerebral cortical necrosis was seen at the mid dose level of the TAXOL treated animals. This may explain the deaths of the animals treated with even higher doses of TAXOL. No cerebral lesions were seen in animals treated with Capxol.

This lack of cerebral or neurologic toxicity is surprising and has significant implications in both the treatment of brain tumors and the ability to achieve high systemic doses ranging from 5–120 mg/kg in rats (equivalent to 30–700 mg/m2 dose in humans).

To summarize, Capxol was considerably less toxic than TAXOL. No TAXOL animals survived at the doses higher than 9 mg/kg. With the exception of an incidental death at 90 mg/kg Capxol, all animals which received Capxol survived at doses up to and including 120 mg/kg. There was a high dose-related effect of Capxol on the male reproductive organs and a suppression in male body weight. Female rats did not demonstrate any toxic effects from the administration of Capxol at doses up to and including 120 mg/kg. These high doses were administered as bolus injections and represent the equivalent of 30–700 mg/m$^2$ dose in humans.

While the invention has been described in detail with reference to certain preferred embodiments thereof, it will be understood that modifications and variations are within the spirit and scope of that which is described and claimed.

That which is claimed is:

1. A method for the administration of a taxane to a subject in need thereof, said method comprising systemically administering a dose in the range of about 30 mg/m$^2$ to about 1000 mg/m$^2$ of said taxane to said subject in a pharmaceutically acceptable formulation substantially free of cremophor, over an administration time of less than 3 hours, without the use of premedication.

2. The method of claim 1, wherein said dose is at least 135 mg/m$^2$.

3. The method of claim 1, wherein said pharmaceutically acceptable formulation is administered as a bolus injection.

4. The method of claim 3, wherein said dose is at least 135 mg/m$^2$.

5. The method of claim 1, wherein said administration period is less than 2 hours.

6. The method of claim 1, wherein said dose is at least 175 mg/m$^2$.

7. A method for the administration of a taxane to a subject in need thereof, said method comprising systemically administering a dose in the range of about 30 mg/m$^2$ to about 1000 mg/m$^2$ of said taxane to said subject in a pharmaceutically acceptable formulation substantially free of cremophor without the use of premedication, with a treatment cycle of no greater than 2 weeks.

8. The method of claim 7, wherein said dose is at least 135 mg/m$^2$.

9. The method of claim 7, wherein said dose is at least 175 mg/m$^2$.

10. The method of claim 7, wherein said administration period is less than 2 hours.

11. The method of claim 7, wherein said pharmaceutically acceptable formulation is administered as a bolus injection.

12. The method of claim 11, wherein said dose is at least 135 mg/m$^2$.

13. The method of claim 11, wherein said dose is at least 175 mg/m$^2$.

14. The method of claim 11, wherein said dose is at least 250 mg/m$^2$.

15. A method for reducing the hematologic toxicity of a taxane in a subject undergoing treatment with taxane, said method comprising systemically administering a dose in the range of about 30 mg/m$^2$ to about 1000 mg/m$^2$ of said taxane to said subject in a pharmaceutically acceptable formulation, wherein said pharmaceutically acceptable formulation is substantially free of cremophor.

16. The method of claim 15, wherein said pharmaceutically acceptable formulation further comprises albumin.

17. A method for reducing the cerebral or neurologic toxicity of taxane in a subject undergoing treatment with taxane, said method comprising systemically administering a dose in the range of about 30 mg/m$^2$ to about 1000 mg/m$^2$ of said taxane to said subject in a pharmaceutically acceptable formulation, wherein said pharmaceutically acceptable formulation is substantially free of cremophor.

18. The method of claim 17, wherein said pharmaceutically acceptable formulation further comprises albumin.

19. A method for treatment of primary tumors in a subject by achieving high local concentration of taxane at the tumor site, said method comprising systemically administering a dose in the range of about 30 mg/m$^2$ to about 1000 mg/m$^2$ of said taxane to said subject in a pharmaceutically acceptable formulation substantially free of cremophor.

20. The method of claim 19, wherein said primary tumors are selected from cancers of prostate, testes, lung, kidney, pancreas, bone, spleen, liver or brain.

21. The method of claim 20, wherein said pharmaceutically acceptable formulation further comprises albumin.

22. A pharmaceutically acceptable formulation of taxane for treatment of primary tumors in a subject which achieves high local concentration of said taxane at the tumor site, said formulation being substantially free of cremophor and comprising taxane in a dose in the range of about 30 mg/m$^2$ to about 1000 mg/m$^2$.

23. The formulation of claim 22, wherein said primary tumors are selected from cancers of prostate, testes, lung, kidney, pancreas, bone, spleen, liver or brain.

24. The formulation of claim 22 further comprising albumin.

25. A pharmaceutically acceptable formulation of taxane according to claim 22, wherein said formulation shows reduced cerebral or neurologic toxicity.

26. A method for treatment of metastatic tumors in a subject by achieving high local concentration of taxane at the site of metastases, said method comprising systemically administering a dose in the range of about 30 mg/m$^2$ to about 1000 mg/m$^2$ of said taxane to said subject in a pharmaceutically acceptable formulation substantially free of cremophor.

27. The method of claim 26, wherein said site of metastases are selected from lung, bone, liver or brain.

28. The method of claim 26, wherein said pharmaceutically acceptable formulation further comprises albumin.

29. A method for treatment of prostatic cancer in a subject by inducing a medical orchiectomy by administering a dose of taxane in the range of about 30 mg/m$^2$ to about 1000 mg/m$^2$ to said subject in a pharmaceutically acceptable formulation substantially free of cremophor.

30. The method of claim 29, wherein said pharmaceutically acceptable formulation further comprises albumin.

31. A unit dosage form comprising a vessel containing a sufficient quantity of taxane to allow systemic administration at a dose in the range of about 30 mg/m$^2$ to about 1000 mg/m$^2$ over an administration period of less than 3 hours.

32. A unit dosage form according to claim 31, wherein said taxane is administered as a non-aqueous formulation, wherein said non-aqueous formulation is substantially free of cremophor.

33. A unit dosage form according to claim 31, wherein said taxane is administered as a dry powder formulation.

34. A lyophilized taxane-containing formulation characterized by the ability to be reconstituted at concentrations greater than 1.3 mg/ml, and remaining stable for at least 3 days.

35. A taxane-containing formulation suitable for administration using standard intravenous infusion tubing, wherein said taxane-containing formulation has a concentration of greater than 1.3 mg/ml.

36. A taxane-containing formulation suitable for delivery of a dose in the range of about 30 mg/m$^2$ to about 1000 mg/m$^2$ with an administration period of less than 3 hrs.

37. A formulation according to claim 36 wherein said dose comprises about 250–300 mg/m$^2$.

38. A formulation according to claim 31 wherein said dose is delivered in a volume of <200 ml.

39. A pharmaceutically acceptable formulation of taxane comprising in the range of about 30 mg/m$^2$ to about 1000 mg/m$^2$ of taxane, wherein said formulation is useful for the reduction of serum testosterone levels in a subject.

40. The method of claim 1, wherein said dose is greater than 80 mg/m$^2$ and up to 700 mg/m$^2$.

41. A unit dosage form according to claim 31, wherein said quantity of taxane is sufficient to allow systemic administration of a taxane dose of greater than 80 mg/m$^2$ and up to 700 mg/m$^2$ over an administration period of less than 3 hours.

42. A formulation according to claim 36, wherein said dose is greater than 80 mg/m$^2$ and up to 700 mg/m$^2$.

43. The method of claim 1 wherein said formulation is free of cremophor.

44. The method of claim 7 wherein said formulation is free of cremophor.

45. The method of claim 15 wherein said formulation is free of cremophor.

46. The method of claim 17 wherein said formulation is free of cremophor.

47. The method of claim 18 wherein said formulation is free of cremophor.

48. The formulation of claim 22, wherein said formulation is free of cremophor.

49. The method of claim 26 wherein said formulation is free of cremopor.

50. The method of claim 29 wherein said formulation is free of cremophor.

51. The unit dosage form of claim 32 wherein said non-aqueous formulation is free of cremophor.

52. The method of claim 1, wherein said administration period is less than 1 hour.

53. The method of claim 7, wherein said administration period is less than 1 hour.

54. The method of claim 1, wherein said dose is at least 250 mg/m$^2$.

55. The method of claim 7, wherein said dose is at least 250 mg/m$^2$.

56. The method of claim 1, wherein said formulation is free of agents which aid recovery from hematologic toxicity of taxane.

57. The method of claim 7, wherein said formulation is free of agents which aid recovery from hematologic toxicity of taxane.

* * * * *